(12) United States Patent
Park et al.

(10) Patent No.: US 11,077,099 B2
(45) Date of Patent: Aug. 3, 2021

(54) ORAL TABLET FORMULATION OF LENALIDOMIDE

(71) Applicant: SAMYANG HOLDINGS CORPORATION, Seoul (KR)

(72) Inventors: Sang Yeob Park, Daejeon (KR); Hye Jung Lim, Daejeon (KR); Sa Won Lee, Seongnam-si (KR); Min Hyo Seo, Yongin-si (KR)

(73) Assignee: SAMYANG HOLDINGS CORPORATION, Seoul (KR)

( * ) Notice: Subject to any disclaimer, the term of this patent is extended or adjusted under 35 U.S.C. 154(b) by 0 days.

(21) Appl. No.: 16/341,682

(22) PCT Filed: Sep. 11, 2017

(86) PCT No.: PCT/KR2017/009928
§ 371 (c)(1),
(2) Date: Apr. 12, 2019

(87) PCT Pub. No.: WO2018/070671
PCT Pub. Date: Apr. 19, 2018

(65) Prior Publication Data
US 2020/0038390 A1    Feb. 6, 2020

Related U.S. Application Data

(63) Continuation of application No. PCT/KR2017/009928, filed on Sep. 11, 2017.

(30) Foreign Application Priority Data

Oct. 14, 2016 (KR) .................. 10-2016-0133746
Sep. 5, 2017 (KR) .................. 10-2017-0113112

(51) Int. Cl.
| A61K 31/454 | (2006.01) |
| A61K 9/20 | (2006.01) |
| A61K 9/28 | (2006.01) |

(52) U.S. Cl.
CPC .......... *A61K 31/454* (2013.01); *A61K 9/2009* (2013.01); *A61K 9/2018* (2013.01);
(Continued)

(58) Field of Classification Search
CPC .................................................. A61K 9/2009
See application file for complete search history.

(56) References Cited

U.S. PATENT DOCUMENTS

| 2011/0140298 A1* | 6/2011 | Politi ................... B07B 4/08 264/121 |
| 2012/0046315 A1 | 2/2012 | Rimkus et al. |
| 2017/0172929 A1 | 6/2017 | Ahn et al. |

FOREIGN PATENT DOCUMENTS

| CN | 103610658 A | 3/2014 |
| CN | 103705485 B | 7/2015 |
| CN | 105534981 A | 5/2016 |
| CN | 105919958 A | 9/2016 |
| CN | 105534981 B | * 8/2018 |
| KR | 10-2015-0116280 A | 10/2015 |

OTHER PUBLICATIONS

Chuyeshov, "Industrial Technology of Drugs," vol. 2, 2002, 8 pages total.
(Continued)

*Primary Examiner* — Benjamin J Packard
(74) *Attorney, Agent, or Firm* — Birch, Stewart, Kolasch & Birch LLP (57) ABSTRACT

The present disclosure relates to an oral tablet composition comprising lenalidomide and a method for preparing the same. More particularly, the present disclosure relates to a tablet-type composition and a method for preparing the same wherein the composition exhibits physicochemical equivalence with lenalidomide preparations of hard capsules, has (Continued)

pH 1.2 the same pharmacological, therapeutic effect in non-clinical studies and bioequivalence studies, and also has improved ease of taking, handling, safety and the like.

11 Claims, 2 Drawing Sheets

(52) U.S. Cl.
CPC .......... *A61K 9/2054* (2013.01); *A61K 9/2059* (2013.01); *A61K 9/28* (2013.01)

(56) References Cited

OTHER PUBLICATIONS

Cruz, "Lenalidomide (Revlimid): A Thalidomide Analogue in Combination With Dexamethasone for the Treatment of All Patients With Multiple Myeloma," Pharmacy and Therapeutics, vol. 41, No. 5, May 2016, pp. 308-313.
Pharmacopoeia, "Site about registration of Drugs in Russia and EAEU (CIS)" State Pharmacopoeia of the Russian Federation, 2013, 4 pages total.
Extended European Search Report, dated Mar. 31, 2020, for European Application No. 17859733.2.

* cited by examiner

Water

ORAL TABLET FORMULATION OF LENALIDOMIDE

TECHNICAL FIELD

The present disclosure relates to an oral tablet composition comprising lenalidomide and a method for preparing the same. More particularly, the present disclosure relates to a tablet-type composition and a method for preparing the same wherein the composition exhibits physicochemical equivalence with lenalidomide preparations of hard capsules, has the same pharmacological, therapeutic effect in non-clinical studies and bioequivalence studies, and also has improved ease of taking, handling, safety and the like.

BACKGROUND ART

Multiple myeloma is a hematologic malignancy characterized by the abnormal differentiation and proliferation of plasma cells. These abnormal plasma cells are called myeloma cells. Myeloma cells make tumors, melt bone to cause pain and breaks, and invade bone marrow to reduce white blood cells, red blood cells and platelet levels, and thereby increase the risk of anemia, infection and bleeding. In addition, myeloma cells produce M protein, the abnormal immune protein, which causes the blood to thicken and leads to hyperviscosity syndrome or renal damage. It is mainly caused in men (black men especially), and people over 65 years old, and the incidence is gradually increasing in Korea recently. The major medicaments for multiple myeloma are bortezomib, thalidomide and lenalidomide. Bortezomib, an injectable drug, is steadily growing in the market. In case of oral drugs, lenalidomide is used more frequently than thalidomide and has been growing rapidly in the market.

Lenalidomide is the next-generation drug of thalidomide, and it has a better therapeutic effect due to its stronger anti-cancer property and immunomodulating ability. It has been reported that the combination of lenalidomide and dexamethasone in patients with relapses or refractory disease has significantly improved disease-free survival time of 13.4 months and overall survival of 38 months. The side effects such as peripheral neuropathy in thalidomide have been almost eliminated. Although the bone marrow suppression side effect has become more serious, it is known that there are no big problems when the leukocyte stimulating factor is administered. Due to these advantages, the market for lenalidomide is rapidly increasing.

Lenalidomide was developed by Celgene as an oral capsule formulation and is being commercialized at doses of 25, 20, 15, 10, 7.5, 5 and 2.5 mg. The brand name in Korea is Revlimid® capsules, and it contains lenalidomide hemihydrate. The Revlimid® capsules, which are hard capsule preparations, are packed in size 0 capsules in all cases of the formulations of 25, 20, 15 and 10 mg. The major axis is about 2.17 cm, which is considerably long and bulky. Therefore, patients may find it somewhat inconvenient to take, particularly older patients. In addition, even when taken with water, the capsule may stick to the throat or esophagus during swallowing. In this case, the capsule may not be detached therefrom even if the patient drinks a large amount of water. If the drug is accidentally released from the capsule, it may cause pain, and in some cases may cause inflammation. If the tablet form having a short length and a small volume is developed, the problems caused by the inconvenient and bulky capsules can be solved and thus the patient can more easily take the drug. That is, the disadvantages of the capsules can be overcome.

In the late 1950s and 1960s, thalidomide was used as an anti-nociceptant for pregnant women, but there were tragic events in which tens of thousands of malformed babies around the world were born due to the side effects of unexpected teratogenicity. Lenalidomide, like thalidomide, has the side effects of teratogenicity, so it is prohibited to administer or treat a female who is pregnant, a female of child-bearing age or a female who may be pregnant. In order to prevent such a side effect, a thick gelatin capsule surrounds the drug when it is prepared as a capsule, so it can be considered that a safe shielding has been achieved. However, in the case of tablets (especially uncoated tablets) the drug is directly present on the surface of the tablets, and there is a possibility that the tablets may be exposed to handlers unrelated to the use. If a patient takes a split dose along the dividing line on the tablet, or if it is broken during taking it out of the PTP package due to weakness, or if it is crumbled due to friability, there is a risk of exposure of the drug to the handler and surrounding people. If the tablets are coated, there is also a risk of exposure to the handler and surrounding people since the coating is not coated in sufficient quantity due to low coating rate so that the drug is exposed on some or many of the portions of the tablet, or the drug is present on the surface of the coating layer because the drug continuously came out during the coating process.

Therefore, unlike the conventional case, a coated tablet in which a sufficient amount of coating agents is applied to completely coat the tablet so that not only the whole tablet is protected with the coating over a certain thickness or more but also the coating can completely shield the drug from the operator or the like, is required.

At the same time, it may be necessary to design and manufacture the drug so as to have the same drug release rate and release pattern as the commercially available capsules that have been clinically proven. For this purpose, it is essential to select the optimal coating pressure so as to establish an appropriate range of hardness, to select appropriate coating agents, and to design the coating system so as to exhibit an appropriate coating rate and a similar dissolution pattern. It may be necessary to not only ensure in vitro physicochemical equivalence in dissolution media of a wide range of pH, but also to present equivalence in in vivo pharmacokinetic tests of biological equivalence using human subjects as well as non-clinical studies using laboratory animals.

CONTENTS OF THE INVENTION

Problems to be Solved

The purpose of the present disclosure is to provide a tablet composition and a method for preparing the same, by changing the formulation of the commercially available hard capsule lenalidomide preparations to a tablet, wherein the tablet is easy to take due to the short length and small volume, the drug and handler can be separated from each other by completely wrapping the whole tablet over a certain thickness by appropriately selecting the coating agent and coating thickness, and the drug can be prevented from leaking out during the coating process. The present disclosure also provides a tablet composition and a method for preparing the same wherein the dissolution pattern is equivalent to that in capsules and thus the tablet composition exhibits equivalence in in vivo tests of laboratory animals and bioequivalence tests, as well as physicochemical equivalence in comparative dissolution tests. Thus, the present disclosure provides a tablet composition and a method for preparing the same, wherein the tablet composition has similar pharmacological efficacy and effect as commercially available capsule preparations and is even more advanced and improved in appearance, convenience of taking and handling, ease of manufacturing, safety and the like.

Technical Means to Solve the Problems

Definition of Terms

Unless expressly stated otherwise, some terms used throughout this specification may be defined as follows.

Unless the context clearly dictates otherwise, throughout the specification the term "comprising" or "containing" means that any element (or component) is included without special limitation, and is not to be construed as an exclusion of any other element (or component).

Also, "lenalidomide" may be a lenalidomide base (a base drug without a salt), or a pharmaceutically acceptable salt or isomer thereof, or mixtures thereof. In each case, it may also be in the form of various hydrates, and in each case it may be in various crystal forms.

For example, it may be various hydrates such as lenalidomide anhydride, hemi-hydrate, monohydrate, dihydrate and trihydrate, etc., various solvates or mixtures thereof.

In addition, the term "micronized" means that it is powdered to a very small size—e.g., an average diameter is micrometers or nanometers.

In order to solve the above problems, the present disclosure provides an oral tablet composition comprising lenalidomide as an active ingredient and at least one pharmaceutically acceptable carrier. More particularly, the present disclosure provides an oral tablet composition wherein the surface of the uncoated tablet is coated with a coating agent.

In an embodiment of the present disclosure, the oral tablet composition may comprise lenalidomide as an active ingredient; a diluent selected from the group consisting of sugars, sugar alcohols, celluloses, starches, inorganic salts and mixtures thereof; a disintegrant selected from the group consisting of a swellable disintegrant, a wettable disintegrant and mixtures thereof; and a lubricant selected from the group consisting of a soluble lubricant, an insoluble lubricant and mixtures thereof; wherein AUC (area under curve) is 140 to 7100 ng·hr/mL and $C_{max}$ is 42 to 2100 ng/mL, but it may not be limited thereto.

In an embodiment of the present disclosure, the dissolution rate of the oral tablet composition may be 1 to 50% when measured at 2.5 minutes in a 900 mL dissolution medium of pH 1.2 by paddle method at 50 revolutions/min, but it may not be limited thereto.

In an embodiment of the present disclosure, the dissolution rate of the oral tablet composition may be 10 to 95% when measured at 5 minutes in a 900 mL dissolution medium of pH 1.2 by paddle method at 50 revolutions/min, but it may not be limited thereto.

In an embodiment of the present disclosure, the disintegration time of the oral tablet composition in a buffer solution of pH 1.2 may be 1 to 20 minutes, but it may not be limited thereto.

In an embodiment of the present disclosure, the hardness of the oral tablet composition may be 10 N to 300 N, and the friability may be less than 2% but it may not be limited thereto.

In an embodiment of the present disclosure, the coating layer of the oral tablet composition may be more than a single layer and/or the total thickness of the coating layer may be at least 1 μm, but it may not be limited thereto.

In an embodiment of the present disclosure, the oral tablet composition may comprise 0.5 to 200 parts by weight of the diluent, 0.02 to 10 parts by weight of the disintegrant and/or 0.005 to 3.5 parts by weight of the lubricant per 1 part by weight of lenalidomide, but it may not be limited thereto.

In an embodiment of the present disclosure, the volume of the tablet may be less than that of a size 0 capsule, but it may not be limited thereto.

The present disclosure also provides a method for preparing the oral tablet composition comprising mixing lenalidomide as an active ingredient and at least one pharmaceutically acceptable carrier; compressing the mixture to prepare a tablet before coating (an uncoated tablet); and coating the surface of the uncoated tablet with a coating agent.

In the present disclosure, the lenalidomide may be used in a micronized form. The average particle size (×50) of the micronized lenalidomide may be, for example, less than 100 μm, preferably less than 50 μm, more preferably less than 30 μm, and even more preferably less than 15 μm. In addition, the average particle size (×50) of the micronized lenalidomide may be, for example, at least 0.1 μm, preferably at least 0.2 μm, more preferably at least 0.5 μm, even more preferably at least 1 μm. If the average particle size of the lenalidomide is not within the above-mentioned range, the dissolution rate may be lowered or the process may be obstructed. The average particle size (×50) means a particle size corresponding to 50% of the weight percentage in the particle size distribution curve, which can be measured using, for example, a light diffraction particle size analyzer.

In the tablet composition of the present disclosure, the pharmaceutically acceptable carrier included in the uncoated tablet may be, for example, at least one selected from a diluent, a disintegrant and a lubricant.

In an embodiment of the present disclosure, the diluent may be selected from the group consisting of sugars, sugar alcohols, celluloses, starches, inorganic salts and mixtures thereof.

In an embodiment of the present disclosure, the disintegrant may be selected from the group consisting of a swellable disintegrant, a wettable disintegrant and mixtures thereof.

Said sugar is a concept encompassing monosaccharides, polysaccharides and pharmaceutically acceptable derivatives thereof; starch is a concept encompassing starches and pharmaceutically acceptable derivatives thereof; and cellulose is a concept encompassing celluloses and pharmaceutically acceptable derivatives thereof, which would be known and available to a skilled artisan, but are not particularly limited to a specific component.

Said diluent may be, for example, at least one selected from the group consisting of lactose (either anhydride or hydrate—e.g., monohydrate), cellulose powder, microcrystalline cellulose, silicified microcrystalline cellulose, starch, gelatinized starch, calcium carbonate, cyclodextrin, calcium sulfate, calcium silicate, magnesium carbonate, dicalcium phosphate, tricalcium phosphate, magnesium trisilicate, potassium chloride, sodium chloride, dibasic calcium phosphate dihydrate, tribasic calcium phosphate, kaolin, magnesium carbonate, magnesium oxide, mannitol, maltitol, sorbitol, xylitol, lactose, dextrose, maltose, sucrose, glucose, fructose, maltodextrin, dextrates, dextrin and mixtures thereof. However, it may not be limited thereto. Preferably, lactose, microcrystalline cellulose, mannitol, starch or mixtures thereof may be selected. Most preferably, a mixture of lactose and microcrystalline cellulose may be selected. The diluent may also act as a binder.

In an embodiment of the present disclosure, 0.5 to 200 parts by weight, preferably 1 to 100 parts by weight, more preferably 2 to 50 parts by weight, still more preferably 3 to 30 parts by weight, even more preferably 4 to 20 parts by weight of the diluent per 1 part by weight of lenalidomide may be used. If the amount of the diluent to be used is much smaller than the above range, it is difficult to prepare the tablets. On the other hand, if the diluent is used in excess of the above range, the concentration of the drug may be lowered, so there may be a problem in securing the content uniformity in the production of tablets.

Said disintegrant may be, for example, selected from the group consisting of starch, cellulose, cross-linked polymer, gums, polysaccharides and mixtures thereof. For example, it may be at least one selected from the group consisting of croscarmellose sodium (CrosCMC-Na), carboxymethylcellulose, crospovidone (cross-linked polyvinylpyrrolidone), low-substituted hydroxypropylcellulose (L-HPC), starch (wheat, rice, corn or potato starch), sodium carboxymethyl starch, sodium starch glyconate, alginic acid, carboxymethylcellulose sodium, agar, xylan, gellan gum, xanthan gum, partially hydrolyzed starch and mixtures thereof. However, it may not be limited thereto. Preferably, the disintegrant may be croscarmellose sodium, crospovidone, low-substituted hydroxypropylcellulose (L-HPC) or sodium starch glyconate. More preferably, the disintegrant may be croscarmellose sodium.

In an embodiment of the present disclosure, 0.02 to 10 parts by weight, preferably 0.05 to 5 parts by weight, more preferably 0.1 to 2.5 parts by weight, still more preferably 0.15 to 1.5 parts by weight, even more preferably 0.2 to 1 part by weight of the disintegrant per 1 part by weight of lenalidomide may be used. If the amount of the disintegrant to be used is much smaller than the above range, there may be a problem of retardation of the dissolution rate due to the retardation of the disintegration rate. On the other hand, if the disintegrant is used in excess of the above range, there may be a problem in productivity such as compressing failure or coating failure.

In an embodiment of the present disclosure, the lubricant may be selected from the group consisting of a soluble lubricant, an insoluble lubricant and mixtures thereof.

Said lubricant is a concept encompassing a lubricant, an antiadherant and a glidant. For example, the lubricant may be at least one selected from the group consisting of magnesium stearate, fumaric acid, stearic acid, calcium stearate, sodium stearyl fumarate, sucrose fatty acid ester, starch (wheat, rice, corn or potato starch), talc, highly dispersed (colloidal) silica, magnesium oxide, magnesium carbonate, glyceryl behenate, glyceryl monostearate, silicon dioxide, calcium silicate, magnesium silicate, hardened vegetable oil, hard liquid paraffin, polyethylene glycol, sodium laurylsulfate, magnesium laurylsulfate, sodium benzoate, polyoxyethylene monostearate, glyceryl triacetate, sucrose monolaurate and mixtures thereof, but it may not be limited thereto. Preferably, the lubricant may be magnesium stearate, stearic acid or highly dispersed (colloidal) silica. More preferably, the lubricant may be magnesium stearate.

In an embodiment of the present disclosure, 0.005 to 3.5 parts by weight, preferably 0.015 to 2.0 parts by weight, more preferably 0.03 to 0.75 part by weight, still more preferably 0.05 to 0.5 part by weight, even more preferably 0.1 to 0.35 part by weight of the lubricant per 1 part by weight of lenalidomide may be used. If the amount of the lubricant to be used is much smaller than the above range, there may be a problem in productivity such as compressing failure. On the other hand, if the lubricant is used in excess of the above range, there may be a problem of retardation of the dissolution or a problem in productivity.

The coating agent may be a hydrophilic polymer, for example, at least one selected from the group consisting of hydroxypropylmethylcellulose (HPMC), polyvinyl alcohol (PVA), Macrogol polyvinyl alcohol graft copolymer, polymer of acrylic acid and its salt, polymethacrylate, poly (butylmethacrylate, 2-dimethylaminoethyl methacrylate, methyl methacrylate) copolymer (for example, Eudragit® E, Evonik), carboxymethyl cellulose (sodium salts and calcium salts), ethyl cellulose, methyl cellulose, hydroxyethyl cellulose, ethyl hydroxyethyl cellulose, hydroxypropyl cellulose (HPC), L-HPC (low-substituted HPC), polyvinyl pyrrolidone (PVP), vinylpyrrolidone-vinylacetate copolymer (for example, Kollidon® VA64, BASF), gelatin, guar gum, partially hydrolyzed starch, alginate, xanthan and mixtures thereof. However, it may not be limited thereto.

Preferably, the coating agent may be hydroxypropylmethylcellulose (HPMC), polyvinyl alcohol (PVA), Macrogol polyvinyl alcohol graft copolymer poly (butylmethacrylate, 2-dimethylaminoethyl methacrylate, methyl methacrylate) copolymer (for example, Eudragit® E, Evonik).

In an embodiment of the present disclosure, 1 to 30 parts by weight, preferably 2 to 25 parts by weight, more preferably 3 to 20 parts by weight, still more preferably 4 to 15 parts by weight, even more preferably 5 to 15 parts by weight, and most preferably 6 to 15 parts by weight of the lubricant per 100 parts by weight of the uncoated tablet may be used. If the amount of the hydrophilic polymer to be used is much smaller than the above range, there may be a problem in that the whole uncoated tablet is not covered by the coating agent. On the other hand, if the hydrophilic polymer is used in excess of the above range, there may be an excessive delay in the dissolution rate.

After cutting the tablet in half, the thickness of the coating layer can be measured by a scanning electron microscope (SEM) or the like. At this time, it is preferable that the whole surface of the tablet be uniformly coated with a certain thickness, and the average thickness can be determined by measuring 5 or more of the tablets and averaging them. When observing a cross section, the average thickness of the coating layer may be at least 1 µm and no more than 300 µm. More preferably, it may be at least 3 µm and no more than 275 µm. Even more preferably, it may be at least 5 µm and no more than 250 µm. Even more preferably, it may be at least 7 µm and no more than 225 µm. Even more preferably, it may be at least 10 µm and no more than 200 µm. Even more preferably, it may be at least 15 µm and no more than 180 µm. Most preferably, it may be at least 20 µm and no more than 150 µm. If the average thickness of the coating layer is thinner than the above range, it is difficult to uniformly coat the entire tablet and dust may be generated during handling. If the average thickness of the coating layer is thicker than the above range, the desired purpose may not be achieved due to the retardation of the dissolution, excessive process time and the like.

When the coating layer is formed as a single layer, one or more coating agents may be mixed and used, and the whole tablet is coated with a sufficient amount of the coating agent so as to form a coating layer. The coating layer may preferably be a double layer or more. For example, in the case of coating with more than a double layer, each layer may be made of a different coating agent to shield the tablet against exposure to the drug, moisture, oxidation and the like. In an embodiment, a primary coating with hydroxypropylmethylcellulose (HPMC) is preferably performed to form a barrier to the drug, and then a secondary coating with Macrogol polyvinyl alcohol graft copolymer is performed to finally form a double-layer coating. In an embodiment, a primary coating with hydroxypropylmethylcellulose (HPMC) is preferably performed to form a barrier to the drug, and then a secondary coating with polyvinyl alcohol (PvA) is performed to form a moisture-proofing barrier so as to finally form a double-layer coating of an improved function. However, it may not be limited thereto.

It may be necessary to carefully choose the type and composition of the solvent used in preparing the coating liquid in order to prevent the drug from being instantaneously dissolved by the coating liquid during coating and being contained in the coating layer. In addition, coating conditions may need to be established to allow the coating solution to dry quickly after being coated to the uncoated tablet. The coating solvent may be, but is not limited to, ethanol, methanol, acetone, acetonitrile, tetrahydrofuran, hexane, methylene chloride, isopropyl alcohol, water or the like, or mixtures thereof. Preferably, ethanol, water or mixtures thereof may be used. More preferably, a mixture of ethanol and water, a mixture of methylene chloride and ethanol, or a mixture of isopropyl alcohol and ethanol is used as a coating solvent to form a primary coating, and then water is used as a coating solvent to form a secondary coating.

During the process for preparing the coated tablet as described above, various further biologically inert ingredients may be used for the additional purpose of improving coating efficiency, drug stability, appearance, color, protection, maintenance, binding, performance and preparing process, etc.

In an embodiment of the present disclosure, the biologically inert ingredient that may be further included in the coating layer may be at least one selected from the group consisting of plasticizers, lubricants, colorants, flavors, surfactants, stabilizers, antioxidants, foaming agents, antifoaming agents, paraffin and wax, etc.

The plasticizers which may further be included in the coating layer are, for example, at least one selected from the group consisting of triethyl citrate, dibutyl phthalate, diethyl phthalate, dibutyl sebacate, diethyl sebacate, tributyl citrate, acetyl triethyl citrate, propylene glycol, triacetin, polyethylene glycol, cetyl alcohol, stearyl alcohol and cetostearyl alcohol, but it may not be limited thereto. The plasticizer may be used in an amount of at least 100% by weight (for example, 0 to 100% by weight or 0.1 to 100% by weight), specifically at least 50% by weight (for example, 0 to 50% by weight or 0.1 to 50% by weight) and more specifically at least 30% by weight (for example, 0 to 30% by weight or 0.1 to 30% by weight) based on the total dry weight of the polymer used for each coating layer, but it may not be limited thereto.

The lubricant which may further be included in the coating layer may be, for example, at least one selected from the group consisting of magnesium stearate, fumaric acid, stearic acid, calcium stearate, sodium stearyl fumarate, polyethylene glycol, starch (wheat, rice, corn or potato starch), talc, highly dispersed (colloidal) silica, magnesium oxide, magnesium carbonate, glyceryl behenate, glyceryl monostearate, silicon dioxide, calcium silicate, magnesium silicate and mixtures thereof, but it may not be limited thereto. The lubricant may be used in an amount of at least 100% by weight (for example, 0 to 100% by weight or 0.1 to 100% by weight) based on the total dry weight of the polymer used for each coating layer, but it may not be limited thereto.

In an embodiment of the present disclosure, after weighing the raw ingredients, the tablet may be prepared in the order of (optional) granulation, mixing, compressing (tableting) and coating. The granulation may be carried out by using a method such as dry granulation, wet granulation and the like.

In an embodiment of the present disclosure, in the case of wet granulation method, granules are obtained by preparing a binder solution, forming granules from a mixture of a drug and a diluent, etc. along with a binder solution, sieving and drying. After that, the remaining ingredients are mixed and then compressed. The binder solution may be prepared by dissolving a water-soluble polymer such as hydroxypropyl methylcellulose (HPMC), polyvinyl alcohol (PVA), hydroxypropyl cellulose (HPC), L-HPC (low-substituted HPC), polyvinylpyrrolidone (PVP), vinylpyrrolidone-vinyl acetate copolymer (e.g., Kollidon® VA64, BASF) or sugars or sugar alcohols such as white sugar, sorbitol, maltitol, xylitol and erythritol, etc. in water, ethanol or a mixed solution thereof.

In an embodiment of the present disclosure, when granulating with a dry granulation method, a mixture of a drug, a diluent and a binder is pressed by using a roller compactor and then sieved. After that, the remaining ingredients are mixed and then compressed.

Direct compression, instead of granulation, is advantageous in a simplified process because the ingredients are mixed and compressed immediately after weighing the raw ingredients. Because the drug itself has teratogenic side effects, it may be necessary to wear protective equipment during the manufacturing process. It may be advisable to exclude pregnant women or women who may be pregnant if possible. In addition, it may be preferable to use direct compression in which exposure of the operator to the drug is minimized. However, the present disclosure may not be limited thereto.

When the ratio of the drug in the tablet is low, it may be important to secure mixing uniformity. Careful attention may therefore be required to ensure mixing uniformity from the mixing step. Mixing uniformity of the mixture can be improved if the drug, diluent, disintegrant and lubricant, etc. are mixed sequentially, not mixed together.

For example, in an embodiment, a portion of the diluent is mixed with the drug, and then a portion of the diluent is further added and mixed. Then, the remaining portion of the diluent is added thereto and mixed, and the disintegrant and the lubricant are added stepwise in order to prepare a mixture for final compression.

For example, in another embodiment, the disintegrant may be first mixed with the drug, and then a portion of the diluent may be added thereto and further mixed. Then, a portion of the diluent is added and further mixed, and the lubricant is lastly added thereto in order to prepare a mixture for final compression.

Since the dose of the drug may vary, it may be necessary to set the shape, weight and size for each tablet and manufacture it with appropriate punches. For each dose, the same type of excipient may be used. In addition, the ratio of the excipient to be used may be varied or the same with respect to each dose. Preferably, by designing all doses of tablets to have the same excipients and the same proportions, the amount of lenalidomide, the amount of each excipient and the total weight of the tablet may be made proportional.

The shape of the tablet may vary, such as a rectangle, an ellipse, a diamond, a circle and a polygon (e.g., a triangle, a tetragon, a pentagon and a hexagon, etc.). The shape of the tablet may be determined in light of ease of use, ease of punch manufacture and management, ease of manufacturing such as tableting, coating, packaging and handling, controllability of the dissolution pattern, and ease of controlling factors related to properties such as hardness, friability and disintegration of the tablet. In addition, a suitable shape can be selected for each dose.

The total weight of the uncoated tablet is preferably such that the average weight of the tablet does not exceed 1100 mg. More preferably it may not exceed 880 mg, still more preferably it may not exceed 660 mg, even more preferably it may not exceed 550 mg, and most preferably it may not exceed 440 mg.

The lower limit of the average of the total weight of the uncoated tablet is preferably at least 5 mg. More preferably it may be at least 10 mg, still more preferably it may be at least 20 mg, even more preferably it may be at least 30 mg, and most preferably it may be at least 40 mg.

The length of the longest axis (in case of circular shape, diameter) of the uncoated tablet is preferably shorter than the length of the No. 0 capsule which is 2.17 cm. More preferably it may be no more than 2 cm, still more preferably it may be no more than 1.8 cm, and even more preferably it may be no more than 1.6 cm.

The length of the shortest axis (in the case of circular shape, diameter) of the uncoated tablet is preferably at least 1 mm. More preferably it may be at least 2 mm, still more preferably it may be at least 3 mm, and even more preferably it may be at least 4 mm.

The hardness of the uncoated tablet may vary depending on the shape, weight and size of tablet, but the maximum average hardness of 300 N and the minimum average hardness of 10 N are preferable. More preferably, the maximum average hardness is 250 N and the minimum average hardness is 20 N. More preferably, the maximum average hardness is 230 N and the minimum average hardness is 30 N. Most preferably, the maximum average hardness is 210 N and the minimum average hardness is 40 N. If the hardness of the uncoated tablet is much higher than the above range, there may be a delay in release of the drug due to the delay of disintegration. On the other hand, if the hardness of the uncoated tablet is lower than the above range, the tablets may be broken during coating, transportation, storage and taking due to weakness.

The above hardness refers to a value measured on the major axis in case of a rectangular tablet, etc., and also refers to an average hardness of 6 randomly selected tablets.

In the present disclosure, the friability of the uncoated tablet may be less than 2%. More preferably, the friability may be less than 1%. Even more preferably, the friability may be less than 0.5%.

In the present disclosure, the disintegration time of the uncoated tablet may be one of the important factors that can determine the release time of the drug. Therefore, it is necessary to have a proper hardness by compressing with an appropriate pressure during the tableting process, so that the tablet can have a desired disintegration time, which may be a factor in determining the dissolution pattern of the tablets in addition to the amount of the coating agent in the coating process. The dissolution pattern affects the absorption in the body. Therefore, it may be important to set an appropriate disintegration time by providing an appropriate hardness by an appropriate tableting pressure. In addition, the dissolution pattern of the drug should be consistent even if the dose is changed. That is, the disintegration time may be consistent for all the tablets having different doses.

The disintegration time may be measured according to the No. 17 disintegration test among the general test methods of Korean Pharmacopeia, tenth edition (KP X), in the pH 1.2 buffer solution which is the first test solution. The disintegration time is determined by measuring 6 tablets and averaging. In an embodiment, the mean disintegration time of the uncoated tablets is 1 to 20 minutes, preferably 1 minute and 30 seconds to 15 minutes, more preferably 2 minutes to 10 minutes, still more preferably 2 minutes 30 seconds to 8 minutes, even more preferably 3 minutes to 6 minutes, and most preferably 3 minutes 30 seconds to 5 minutes 30 seconds. In the present disclosure, the coating layer formed on the uncoated tablet may be a single layer, a double layer or more, more preferably a double layer or more.

The solvent for the coating may vary. For example, for HPMC coating, the solvent may have anhydrous ethanol and water in a ratio of between 2:8 and 8:2, or may be water alone. Further, for example, water can be used alone as a solvent for PVA coating. All these solvents volatilize during the coating process and do not substantially remain in the final product.

The tablets may further contain various additives in order to improve the physical properties of the tablets, the productivity, the compressibility, the appearance, the taste and/or the stability of the drug, and the like. Such additives include, for example, stabilizers, solubilizers, sweeteners, flavor enhancers, pigments, wetting agents, fillers, stabilizers, surfactants, lubricants, solubilizers, buffers, adsorbents, flavor enhancers, binders, suspending agents, hardeners, antioxidants, glazing agents, flavoring agents, flavors, coating agents, wetting agents, moisture controlling agents, fillers, defoaming agents, refreshing agents, masticatories, antistatic agents, colorants, sugars, isotonic agents, softeners, emulsifiers, crosslinking agents, viscosity increasing agents, forming agents, pH adjusters, excipients, dispersing agents, disintegrants, waterproofing agents, anti-microbial agents, preservatives, solubilizing agents, solubilizers, solvents and fluidizers, etc. However, it is not limited thereto and any additives can be used if they are pharmaceutically acceptable. The coated tablets of the present disclosure may exhibit a dissolution rate in the dissolution test which is equivalent to that of the comparative preparation made into capsules. In particular, the initial dissolution rate at 2.5 minutes, 5 minutes, 10 minutes and 15 minutes, etc. is important in an acidic condition such as a buffer solution of pH 1.2.

The dissolution test can be carried out according to the No. 35 dissolution test among the general test methods of Korean Pharmacopeia, tenth edition (KP X), by the paddle method which is the second method, at 50 revolutions/min at 37° C. The average dissolution rate at certain time points can be obtained by testing each of six (6) tablets and measuring their dissolution rate at each time point by HPLC.

The average dissolution rate of lenalidomide from the coated tablet at each time point may be, for example, 1 to 50% at 2.5 minutes, 10 to 95% (or 20 to 90%) at 5 minutes, 40% to 105% at 10 minutes or 70% to 105% at 15 minutes.

In an embodiment, the coated tablet may have the average dissolution rate of preferably 2 to 48%, more preferably 5 to 45%, and even more preferably 10 to 40% when measured at 2.5 minutes in 900 mL dissolution medium of pH 1.2 by the paddle method at 50 revolutions/min.

In an embodiment, the coated tablet may have the dissolution rate of preferably 20 to 90%, more preferably 30 to 87.5%, still more preferably 40 to 85%, and even more preferably 50 to 80% when measured at 5 minutes in 900 mL dissolution medium of pH 1.2 by the paddle method at 50 revolutions/min. In an embodiment, the coated tablet may have the dissolution rate of preferably at least 50%, more preferably at least 60%, still more preferably at least 70%, and even more preferably at least 80% when measured at 10 minutes in 900 mL dissolution medium of pH 1.2 by the paddle method at 50 revolutions/min.

In an embodiment, the coated tablet may have the dissolution rate of preferably at least 75%, more preferably at least 77.5%, still more preferably at least 80%, and even more preferably at least 85% when measured at 15 minutes in 900 mL dissolution medium of pH 1.2 by the paddle method at 50 revolutions/min.

The coated tablet may have AUC (area under curve) and $C_{max}$ (maximum blood concentration) values which are 80 to 125%, preferably 90 to 110%, and most preferably 95 to 105% when compared to capsule preparations, in the bioequivalence test (in vivo PK test).

In a bioequivalence test conducted on healthy volunteer adults (males), the AUC (area under curve) as a pharmacokinetic factor may be 140 to 7100 ng·hr/mL. It may be preferably 280 to 5700 ng·hr/mL, more preferably 425 to 4250 ng·hr/mL, still more preferably 570 to 2800 ng·hr/mL, even more preferably 700 to 2100 ng·hr/mL, and most preferably 1000 to 1800 ng·hr/mL.

In a bioequivalence test conducted on healthy volunteer adults (males), the $C_{max}$ as a pharmacokinetic factor may be 42 to 2100 ng/mL. It may be preferably 84 to 1680 ng/mL, more preferably 120 to 1260 ng/mL, still more preferably 160 to 840 ng/mL, even more preferably 210 to 630 ng/mL, and most preferably 310 to 525 ng/mL.

The tablet composition of the present disclosure as described above may be used for the same uses as the previous lenalidomide preparations—for example, for treating and/or preventing multiple myeloma, bone marrow dysplasia syndrome and the like.

Effects of the Invention

The tablet composition comprising lenalidomide disclosed in the present disclosure presents physicochemical equivalence with lenalidomide preparations of hard capsules, has the same pharmacological therapeutic effect in non-clinical studies and bioequivalence studies, and also has improved ease of taking, handling, safety and the like, and thus it is expected to be useful as a tablet-form composition.

DETAILED DESCRIPTION TO CARRY OUT THE INVENTION

The present invention is explained in more detail by the following examples. However, these examples seek to illustrate the present invention only, and the scope of the present invention is not limited by the examples in any manner.

Example 1

<Preparation of Uncoated Tablets>

5.0 g of lenalidomide and 40.0 g of anhydrous lactose were sieved and mixed. Thereafter, 31.8 g of microcrystalline cellulose, 2.4 g of croscarmellose sodium and 0.8 g of magnesium stearate were sieved and finally mixed. The mixture was compressed by using a oblong punch, based on 400 mg weight per tablet. The hardness of the uncoated tablet was about 155 N.

<Coating of the Uncoated Tablets>

The above-prepared uncoated tablet was double-coated with two types of coating agents in an amount of total of 7.5% (w/w) based on 100% (w/w) of the total weight of the uncoated tablet. After primary coating (2.5% (w/w)) with Opadry® containing HPMC as a main component, secondary coating (5% (w/w)) was performed with Opadry® containing PVA as a main component. The primary coating operation conditions are shown in Table 1 below, and the secondary coating operation conditions are shown in Table 2 below.

TABLE 1

| Time | Temperature | Inlet Temp | Outlet Temp | Air Pressure | Fan Speed | Injection rate |
|---|---|---|---|---|---|---|
| warming up: 10 min | 40 | 56 | 32 | — | 10 | — |
| Condition | 38 | 56 | 32 | 0.1 | 10 | 4~5 |

TABLE 2

| Time | Temperature | Inlet Temp | Outlet Temp | Air Pressure | Fan Speed | Injection rate |
|---|---|---|---|---|---|---|
| warming up: 10 min | 45 | 66 | 34 | — | 10 | — |
| Condition | 45 | 66 | 34 | 0.1 | 10 | 2.0 |

Example 2

<Preparation of Uncoated Tablets>

5.0 g of lenalidomide and 40.0 g of anhydrous lactose were sieved and mixed. Thereafter, 31.8 g of microcrystalline cellulose, 2.4 g of croscarmellose sodium, 0.4 g of magnesium stearate, 0.2 g of Aerosil and 0.2 g of stearic acid were sieved and finally mixed. The mixture was compressed by using a oblong punch, based on 400 mg weight per tablet. The hardness of the uncoated tablet was 150 N.

<Coating of the Uncoated Tablets>

The above-prepared uncoated tablet was double-coated with two types of coating agents in an amount of total of 6% (w/w) based on 100% (w/w) of the total weight of the uncoated tablet. After primary coating (2% (w/w)) with Opadry® containing HPMC as a main component, secondary coating (4% (w/w)) was performed with Opadry® containing Macrogol polyvinyl alcohol graft copolymer as a main component.

Example 3

<Preparation of Uncoated Tablets>

5.0 g of lenalidomide and 40.0 g of spray-dried mannitol were sieved and mixed. Thereafter, 31.8 g of microcrystalline cellulose, 2.4 g of sodium starch glycolate and 0.8 g of calcium stearate were sieved and finally mixed. The mixture was compressed by using a oblong punch, based on 400 mg weight per tablet. The hardness of the uncoated tablet was 165 N.

<Coating of the Uncoated Tablets>

The above-prepared uncoated tablet was coated with Opadry® containing HPMC as a main component in an amount of total of 5% (w/w) based on 100% (w/w) of the total weight of the uncoated tablet.

Experimental Example 1: Measurement of Properties of the Tablets

Friability Test

Friability was measured for 10 tablets by the method described in US Pharmacopoeia 1216 Tablet Friability item using a Pharmatest friability tester, and the results are shown in Table 3 below (measurement time=4 minutes).

TABLE 3

|  | Friability |
| --- | --- |
| Example 1 (uncoated tablet) | 0.02% |
| Example 2 (uncoated tablet) | 0.02% |
| Example 3 (uncoated tablet) | 0.01% |

Disintegration Test

According to the disintegration test method of Korean Pharmacopeia, tenth edition, the disintegration test was performed for Example 1 in pH 1.2 solution with n=3, and the results are shown in Table 4 below.

TABLE 4

|  | Disintegration time |
| --- | --- |
| Example 1 (uncoated tablet) | 4 min 25 sec |
| Example 2 (uncoated tablet) | 4 min 38 sec |
| Example 3 (uncoated tablet) | 4 min 45 sec |

Experimental Example 2: Dissolution Test

The dissolution test was performed for Example 1 under the following conditions with n=6, and the results are shown in Table 5 below.

TABLE 5

|  | Dissolution rate |
| --- | --- |
| Example 1 (coated tablet) | 94.1% |
| Example 2 (coated tablet) | 92.5% |
| Example 3 (coated tablet) | 95.4% |

Test method: paddle method of dissolution test in Korean Pharmacopoeia

Dissolution medium: 0.01 N HCl solution

Rotation speed: 50 rpm

Temperature: 37

Criterion of time for dissolution: 15 minutes

Analysis method: HPLC method

HPLC analysis conditions

Detector: Ultraviolet absorptiometer (wavelength 210 nm)

Column: 250 mm in length, 4.6 mm in diameter, 5 μm C18 column or equivalent column Flow rate: 1.0 mL/min Injection volume: 10 μL Mobile phase: shown in Table 6 below

TABLE 6

| Time (min) | Solvent A (volume %) | Solvent B (volume %) |
| --- | --- | --- |
| 0.0 | 80 | 20 |
| 11.5 | 80 | 20 |
| 12.0 | 20 | 80 |
| 17.0 | 20 | 80 |
| 17.5 | 80 | 20 |
| 25.0 | 80 | 20 |

Solvent A: A solution wherein 1.36 g of potassium dihydrogen phosphate is dissolved in 1000 mL of water, the pH thereof is adjusted to 3.5±0.05 using orthophosphate and then filtered.

Solvent B: A solution wherein methanol and acetonitrile were mixed at a ratio of 90:10 (v/v) and then filtered.

Experimental Example 3: Comparative Dissolution

The dissolution rate depending on time was measured in pH 1.2, pH 4.0, pH 6.8 and water, according to the dissolution test method among the general test methods of Korean Pharmacopoeia, eighth edition, by using Example 1 and Comparative Example 1 (Revlimid® capsule preparation).

Figure 1:
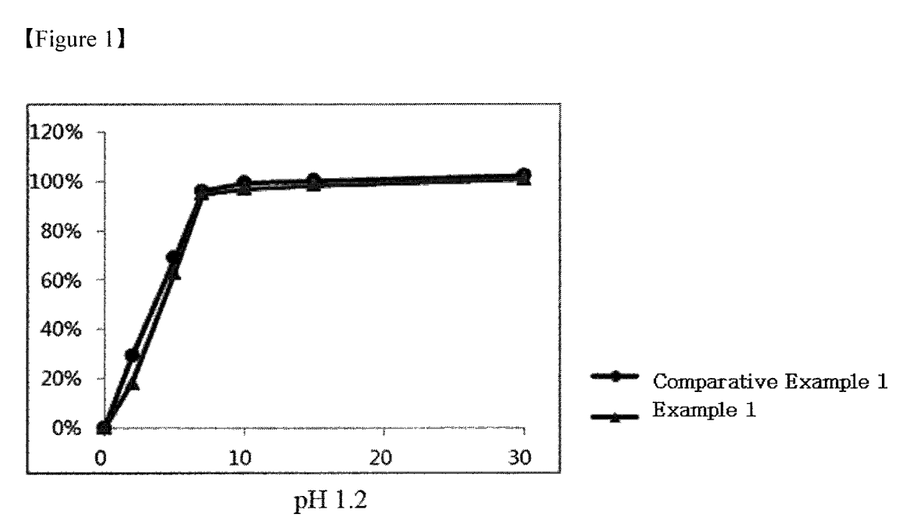
FIG. 1 is a graph showing the result of the comparative dissolution test using the tablet of Example 1 and the capsule preparation of Comparative Example 1 (Revlimid® capsule) in a dissolution medium of pH 1.2.
Figure 2:
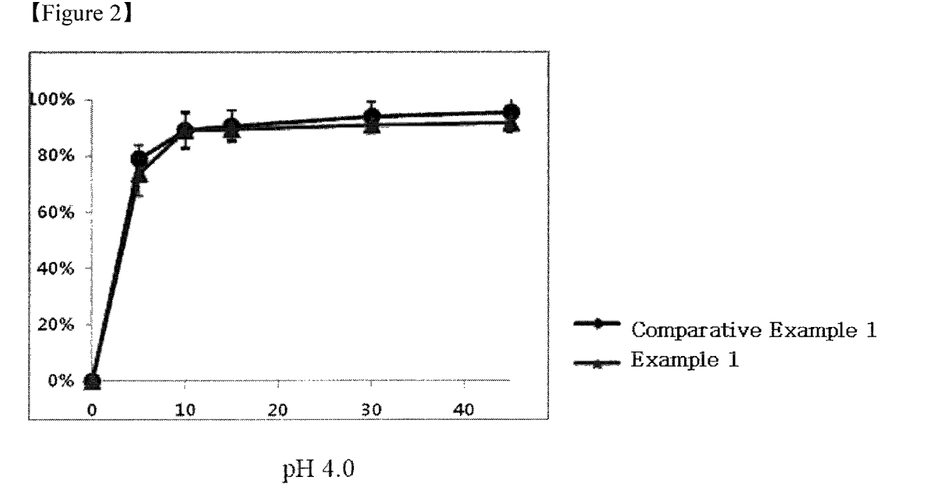
FIG. 2 is a graph showing the result of the comparative dissolution test using the tablet of Example 1 and the capsule preparation of Comparative Example 1 in a dissolution medium of pH 4.0.
Figure 3:
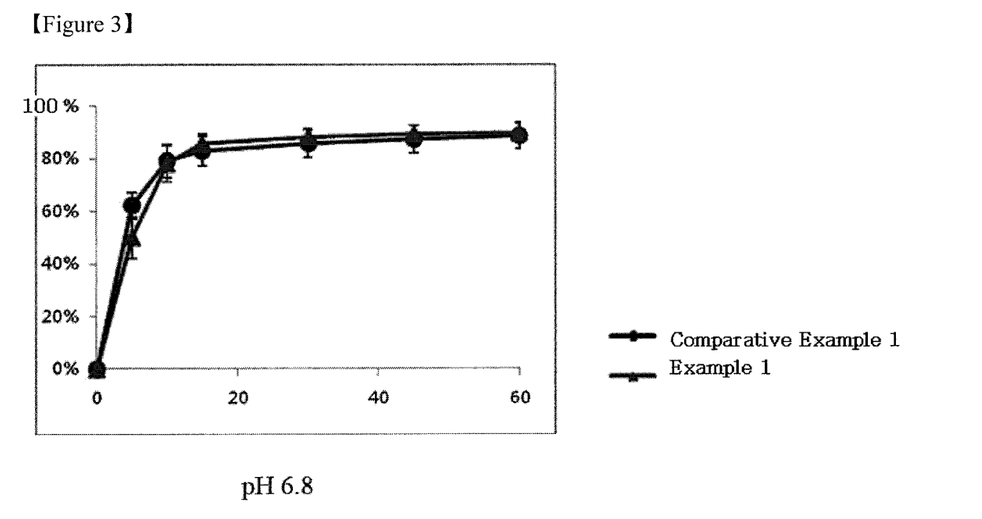
FIG. 3 is a graph showing the result of the comparative dissolution test using the tablet of Example 1 and the capsule preparation of Comparative Example 1 in a dissolution medium of pH 6.8.
Figure 4:
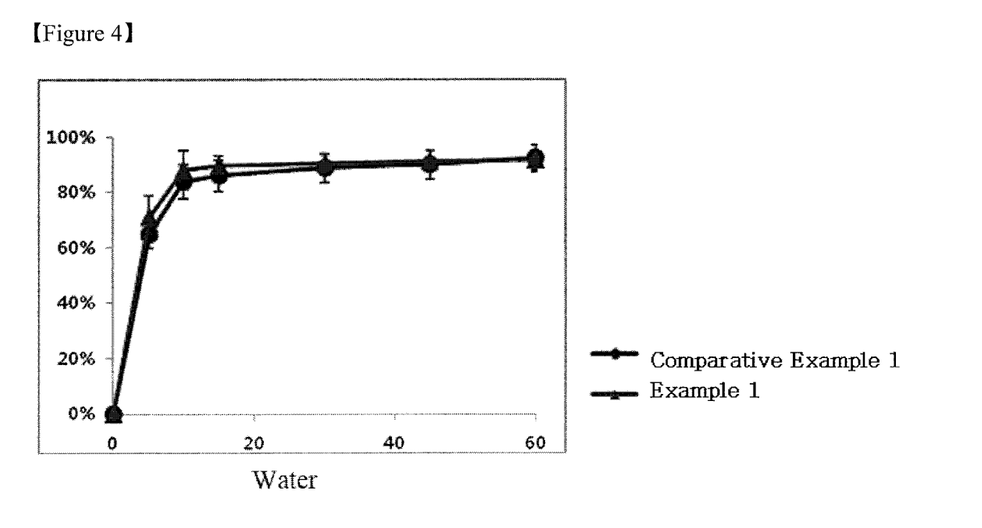
FIG. 4 is a graph showing the result of the comparative dissolution test using the tablet of Example 1 and the capsule preparation of Comparative Example 1 in water.

The dissolution rate was measured by a liquid chromatograph using the test solution taken at each dissolution time, and the dissolution profile is shown in FIGS. 1 to 4.

<Dissolution Conditions>

Device for dissolution test: paddle method of dissolution test in Korean Pharmacopoeia Test solution: pH 1.2, pH 4.0, pH 6.8 and water Rotation speed: 50 rpm Temperature: 37

Criteria of time for dissolution:

2.5, 5, 10, 15 and 30 min (pH 1.2)

5, 10, 15, 30 and 45 min (pH 4.0)

5, 10, 15, 30, 45 and 60 min (pH 6.8 and water)

Analysis method: HPLC method

Example 4: Thickness of the Coating Layer Depending on the Coating Rate

Tablets were compressed into oblong shape so as to have a major axis of 15 mm and a minor axis of 5.8 mm in the same manner as in Example 1, and coated with Opadry® (containing PVA) to prepare tablets each having a certain hardness. The coating rate can be determined from the amount of weight increase after coating compared to the tablet weight.

The average thickness of the coating layer was observed by scanning electron microscopy (SEM) after cutting the tablets in half, and the average of five thickness values was recorded and shown in Table 7 below.

TABLE 7

| Coating rate | Disintegration time (min:sec) | Average thickness of the coating layer (μm) |
|---|---|---|
| 0% (uncoated tablet) | 2:20 | 0.0 |
| 5% | 3:24 | 60.6 |
| 9% | 3:54 | 85.7 |
| 13% | 4:41 | 122.6 |
| 21% | 8:28 | 154.2 |
| 32% | 10:07 | 309.2 |

Example 5: Preparation of Tablets Each Having a Certain Dose of Lenalidomide

Tablets of each dose were prepared in substantially the same manner as in Example 1.

The results of the evaluation for each tablet are shown in Table 8 below.

TABLE 8

| Items | 25 mg | 20 mg | 15 mg | 10 mg | 7.5 mg | 5 mg | 2.5 mg |
|---|---|---|---|---|---|---|---|
| Hardness (N) | 153 | 200 | 170 | 140 | 93 | 80 | 50 |
| Friability (%) | 0.02 | 0.02 | 0.01 | 0.01 | 0.01 | 0.01 | 0.01 |
| Thickness of coating layer (μm) | 52.1 | 64.8 | 40.2 | 56.5 | 38.0 | 33.4 | 31.9 |

Experimental Example 4: Biological Equivalence Test of Lenalidomide

A biological equivalence test was performed on forty-one (41) healthy male volunteers for comparing the test substance lenalidomide tablets (25 mg dose) prepared in Example 1 and the comparative substance Revlimid® (Celgene, 25 mg dose).

The subjects were divided into two groups, the test substance and the comparative substance were taken with water in the fasting condition, and blood was collected at predetermined time intervals up to 24 hours. After 2 weeks, the same drugs were tested but the group was changed. The blood was collected, plasma was separated from the collected blood samples, and they were stored frozen. The samples were analyzed by an LC/MS/MS device to obtain blood concentration. The AUC and $C_{max}$ were obtained from the data, and the results were summarized in Table 9 below.

TABLE 9

| Items | AUC | $C_{max}$ |
|---|---|---|
| Comparative substance | 1416.7 | 420.564 |
| Test substance | 1366.9 | 420.334 |
| Test substance/ Comparative substance | 0.9648 | 0.9995 |

The invention claimed is:

1. An oral tablet composition, comprising:
   lenalidomide as an active ingredient;
   a diluent selected from the group consisting of sugars, sugar alcohols, celluloses, starches and mixtures thereof;
   a disintegrant selected from the group consisting of croscarmellose sodium, sodium starch glyconate and mixtures thereof; and
   a lubricant selected from the group consisting of magnesium stearate, calcium stearate, sodium stearyl fumarate and mixtures thereof;
   wherein 3 to 30 parts by weight of the diluent, 0.1 to 2.5 parts by weight of the disintegrant and 0.03 to 0.75 part by weight of the lubricant per 1 part by weight of lenalidomide are comprised;
   AUC (area under curve) is 140 to 7100 ng·hr/mL;
   $C_{max}$ is 42 to 2100 ng/mL;
   the disintegration time in a buffer solution of pH 1.2 is 2 to 10 minutes; and
   the tablet is a direct compression tablet.

2. The oral tablet composition according to claim 1, wherein a dissolution rate is 1 to 50% when measured at 2.5 minutes in 900 mL dissolution medium of pH 1.2 by a paddle method at 50 revolutions/min.

3. The oral tablet composition according to claim 2, wherein the dissolution rate at 5 minutes is 10 to 95%.

4. The oral tablet composition according to claim 1, wherein a hardness is 10 N to 300 N.

5. The oral tablet composition according to claim 1, wherein a friability is less than 2%.

6. The oral tablet composition according to claim 1, wherein the composition is in the form of a tablet and the tablet is coated with a coating agent.

7. The oral tablet composition according to claim 6, wherein the coating layer is more than a single layer.

8. The oral tablet composition according to claim 6, wherein a total thickness of the coating layer is no less than 1 μm.

9. The oral tablet composition according to claim 6, wherein the coating agent is selected from the group consisting of polyvinylpyrrolidone, hydroxypropylmethylcellulose, carboxymethylcellulose and salts thereof, ethylcellulose, methylcellulose, hydroxyethylcellulose, ethylhydroxyethylcellulose, hydroxypropylcellulose, low-substituted hydroxypropylcellulose, polyvinyl alcohol, Macrogol polyvinylalcohol graft copolymer, polymer of acrylic acid and its salt, polymethacrylate, poly(butylmethacrylate, 2-dimethylaminoethyl methacrylate, methyl methacrylate) copolymer, vinylpyrrolidone-vinyl acetate copolymer, gelatin, guar gum, partially hydrolyzed starch, alginate, xanthan and mixtures thereof.

10. The oral tablet composition according to claim 1, wherein the diluent is selected from the group consisting of lactose, cellulose powder, microcrystalline cellulose, silicified microcrystalline cellulose, starch, gelatinized starch, calcium carbonate, cyclodextrin, mannitol, maltitol, sorbitol, xylitol, lactose, dextrose, maltose, sucrose, glucose, fructose, maltodextrin, dextrates, dextrin and mixtures thereof.

11. The oral tablet composition according to claim 1, wherein the composition is in the form of a tablet and the volume of the tablet is less than that of a size 0 capsule.

* * * * *